United States Patent [19]
Takahashi et al.

[11] Patent Number: 5,576,467
[45] Date of Patent: Nov. 19, 1996

[54] METHOD OF PREPARING AN ALCOHOL

[75] Inventors: Kyoko Takahashi; Makoto Shibagaki; Hajime Matsushita, all of Yokohama, Japan

[73] Assignee: Japan Tobacco Inc., Tokyo, Japan

[21] Appl. No.: 476,327

[22] Filed: Jun. 7, 1995

Related U.S. Application Data

[63] Continuation of Ser. No. 109,268, Aug. 20, 1993, abandoned.

[30] Foreign Application Priority Data

Aug. 21, 1992 [JP] Japan .................................. 4-244050

[51] Int. Cl.$^6$ ........................... C07C 27/04; C07C 29/16; C07C 31/34
[52] U.S. Cl. ..................... 568/885; 568/797; 568/799; 568/841; 568/842; 568/843
[58] Field of Search .................................. 568/797, 799, 568/841, 842, 843, 885

[56] References Cited

U.S. PATENT DOCUMENTS

| | | |
|---|---|---|
| 4,783,559 | 11/1988 | Matsushita et al. . |
| 4,810,825 | 3/1989 | Matsushita et al. . |
| 4,877,909 | 10/1989 | Misusaki et al. . |
| 4,880,037 | 11/1989 | Matsushita et al. . |
| 4,910,177 | 3/1990 | Matsushita et al. . |
| 5,010,052 | 4/1991 | Quemere . |
| 5,082,820 | 1/1992 | Mitsui et al. . |
| 5,171,551 | 12/1992 | Quemere . |

FOREIGN PATENT DOCUMENTS

| | | | |
|---|---|---|---|
| 95408A1 | 5/1983 | European Pat. Off. . | |
| 72091A1 | 2/1986 | European Pat. Off. . | |
| 0281627 | 9/1986 | European Pat. Off. . | |
| 244301 | 4/1987 | European Pat. Off. . | |
| 0239993 | 10/1987 | European Pat. Off. . | |
| 0271092 | 6/1988 | European Pat. Off. . | |
| 0285786 | 10/1988 | European Pat. Off. . | |
| 0370523 | 5/1990 | European Pat. Off. . | |
| 3217429A1 | 8/1982 | Germany . | |
| 52-156192 | 12/1977 | Japan . | |
| 54-32191 | 3/1979 | Japan . | |
| 57-32237 | 2/1982 | Japan . | |
| 58-117887 | 7/1983 | Japan . | |
| 58-143838 | 8/1983 | Japan . | |
| 58-151327 | 9/1983 | Japan . | |
| 58-216131 | 12/1983 | Japan . | |
| 61-204143 | 9/1986 | Japan . | |
| 62-252737 | 11/1987 | Japan . | |
| 63-141937 | 6/1988 | Japan . | |
| 64-15136 | 1/1989 | Japan . | |
| 1218634 | 8/1989 | Japan . | |
| 236136 | 2/1990 | Japan . | |
| 236135 | 2/1990 | Japan . | |
| 3128334 | 5/1991 | Japan . | |
| 3220143 | 9/1991 | Japan . | |
| 356731 | 9/1931 | United Kingdom | 568/885 |
| 800847 | 9/1958 | United Kingdom | 568/885 |

*Primary Examiner*—Alan Siegel
*Attorney, Agent, or Firm*—Birch, Stewart, Kolasch & Birch, LLP

[57] ABSTRACT

The present invention relates to a method of preparing an alcohol by reducing a carboxylic acid or a derivative thereof, more particularly, a method of preparing an alcohol by a reduction reaction in the presence of a zirconium-titanium oxide catalyst. A carboxylic acid or a carboxylic acid derivative is converted into a corresponding alcohol by a reduction reaction in the presence of a zirconium-titanium oxide catalyst using an alcohol as a hydrogen source. An alcohol can be prepared in a high yield in the present invention. To be more specific, the method of the present invention can convert a higher fatty acid or a carboxylic acid derivative, which has given a corresponding alcohol in a low yield in the presence of a zirconium catalyst alone, into the corresponding alcohol in a high yield. Further, the reaction can be performed easily, and the product can be easily separated from the catalyst.

18 Claims, 1 Drawing Sheet

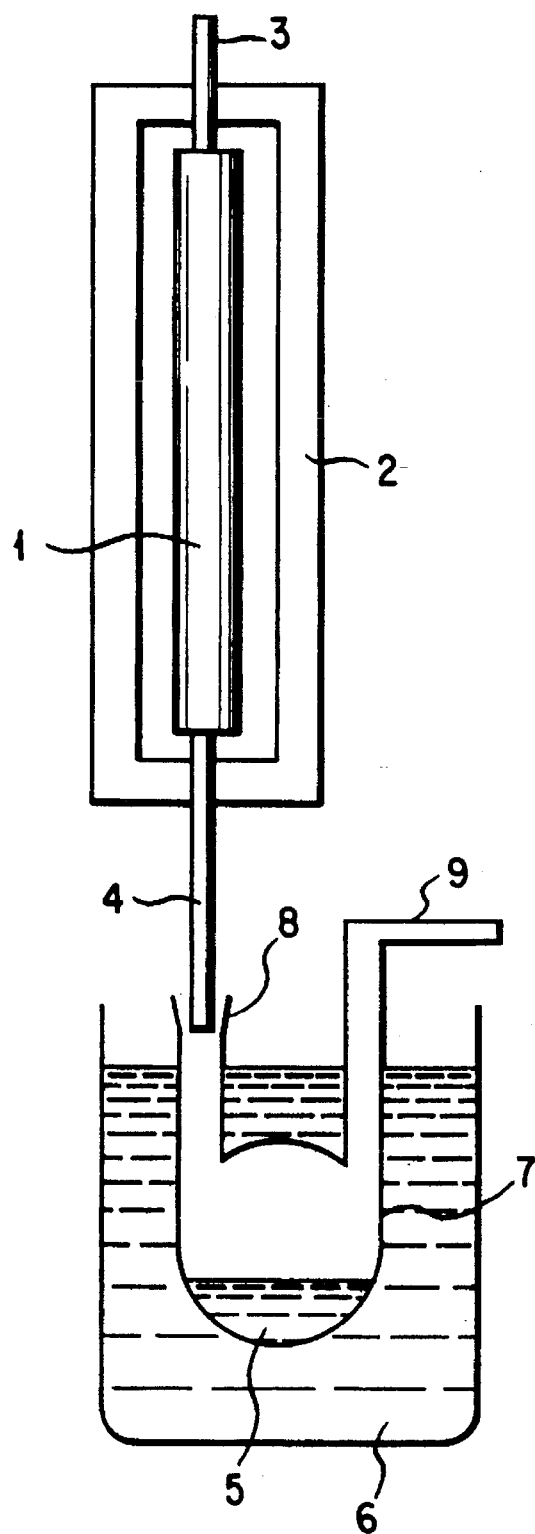
F I G. 1

METHOD OF PREPARING AN ALCOHOL

This application is a continuation of application Ser. No. 08/109,268 filed on Aug. 20, 1993, now abandoned.

BACKGROUND OF THE INVENTION

1. Field of the Invention

The present invention relates to a method of converting a carboxylic acid or a carboxylic acid derivative into the corresponding alcohol.

2. Description of the Related Art

Hitherto, various studies have been conducted on methods of preparing an alcohol from a carboxylic acid or a carboxylic acid ester by use of hydrogen.

A method of preparing a corresponding alcohol from a carboxylic acid is known in which the carboxylic acid is reduced by hydrogen using a rhenium catalyst system (Jpn. Pat. Appln. KOKAI Publication No. 57-32237). However, the method using the rhenium catalyst system is not a general one since it requires high pressure in the range of 50 to 500 arm, and a special apparatus, which involves a high cost.

Among the catalyst which can be used in a method of preparing an alcohol from a carboxylic acid ester, there are, besides the rhenium catalyst, copper-metal oxide catalyst systems, such as copper chromite, copper-zinc oxide, copper-molybdenum oxide, copper ferric oxide, and copper-zirconium oxide (Jpn. Pat. Appln. KOKAI Publication Nos. 63-141937, 2-36135, 3-220143, 54-32191, 52-156192 or 3-128334). Catalysts other than the copper catalyst systems have been proposed. Examples are a nickel catalyst which incorporates tin, germanium, or lead (EP-A-172091), a rhodium catalyst which incorporates tin, germanium, or lead (EP-A-95408 or Jpn. Pat. Appln. KOKAI Publication No. 58-216131), a catalyst consisting of rhenium and a group VIII noble metal (DE-A-3217429), and the like. Catalysts which contain palladium and zinc oxide, or rhenium and zinc oxide on a carrier have also been proposed (Jpn. Pat. Appln. KOKAI Publication No. 2-36136). Using the above-mentioned catalysts, the corresponding alcohol can be obtained from a carboxylic acid ester by reduction with hydrogen gas.

Also known are a method in which a carboxylic acid or a carboxylic acid ester is reduced by using an alcohol as a hydrogen source to produce an alcohol (Jpn. Pat. Appln. KOKAI Publication No. 64-15136), and a method in which an aldehyde or a ketone is reduced to produce an alcohol in the presence of a homogeneous catalyst (Jpn. Pat. Appln. KOKAI Publication Nos. 61-204143 and 62-252737).

Further known is a reduction method by electrolysis (Jpn. Pat. Appln. KOKAI Publication No. 58-117887). This method can be applied only to preparing para-substituted benzyl alcohol. The alcohols corresponding to other carboxylic acids cannot be obtained in this method.

As described above there are various methods of preparing alcohol by reduction. The reduction method using a hydrogen gas, in particular, needs to be performed under relatively high temperature and high pressure. This condition involves high-cost equipment and is dangerous due to inflammable hydrogen gas. The cost and safety problems can be avoided in a reduction method using an alcohol as a hydrogen source, but a restricted source of usable carboxylic acid is another problem. For instance, the alcohol corresponding to a long chain carboxylic acid cannot be obtained in an acceptable yield in this method.

SUMMARY OF THE INVENTION

An object of the present invention is to provide a method of preparing alcohol from a carboxylic acid of a high molecular weight or a derivative thereof, safely and in a high yield.

This object can be attained by a method of preparing an alcohol by converting a carboxylic acid or a carboxylic acid derivative into the corresponding alcohol using alcohol as a hydrogen source in the presence of a catalyst, which is a zirconium-titanium oxide catalyst having an atomic molar ratio of zirconium to titanium in the range of 1:0.3 to 1:1.0.

According to the present invention, a carboxylic acid or a carboxylic acid derivative can be converted into the corresponding alcohol in a high yield and with high selectivity.

To be more specific, the method of the present invention can convert a higher carboxylic acid or a carboxylic acid derivative which has given a corresponding alcohol in a low yield in the present of a hydrous zirconium oxide catalyst alone into the corresponding alcohol in a high yield.

Furthermore, the method of the present invention is advantageous in that the reaction can be performed easily and a product can be easily separated from the catalyst.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWING

The accompanying drawing, which is incorporated in and constitutes a part of the specification, illustrates presently preferred embodiments of the invention and, together with the general description given above and the detailed description of the preferred embodiments given below, serves to explain the principles of the invention.

FIG. 1 is a schematic view of an apparatus for a gas-solid phase reaction which is one of the embodiments of the method of the present invention.

DETAILED DESCRIPTION OF THE PREFERRED EMBODIMENTS

The present invention is characterized in that a zirconium-titanium oxide catalyst is used. Hereinbelow, the catalyst will be described in detail.

The zirconium-titanium oxide catalyst for use in the present invention can be prepared from a mixture of a zirconium salt and a titanium salt. For example, the zirconium salt and the titanium salt are dissolved in a solvent such as deionized water. To this solution are added aqueous ammonia and the like to convert the solution to an alkaline solution, thereby to coprecipitate zirconium hydroxide and titanium hydroxide. The thus obtained coprecipitate is dried and heated to give the above-mentioned zirconium-titanium oxide catalyst. By virtue of the above-mentioned method, the zirconium-titanium oxide catalyst can be readily obtained at a low cost. The thus obtained zirconium-titanium oxide catalyst is a heat-stable, white solid, and is insoluble in water, alcohol and other organic solvents.

The zirconium-titanium oxide catalyst can be used in a reduction method using an alcohol as a hydrogen source. When the zirconium-titanium oxide catalyst is used in a reduction of a carboxylic acid or a carboxylic acid derivative, this catalyst works as a highly active heterogeneous catalyst.

The zirconium salt and the titanium salt for use in preparation of the above-mentioned zirconium-titanium oxide catalyst are not particularly restricted as long as they are soluble in water. As a zirconium salt, oxyzirconium chloride, oxyzirconium acetate, zirconium chloride, zirconium nitrate, and the like are preferably used. Titanium chloride, and the like are preferably used as a titanium salt.

A mixed proportion of a zirconium salt to a titanium salt is preferably from 1:0.3 to 1:1.0 in terms of the atomic molar ratio of zirconium to titanium. In a proportion outside the above-mentioned range, the activity of the obtained catalyst is low. The activity of the zirconium-titanium oxide catalyst produced in a proportion outside the above-mentioned range is lower than that of hydrous zirconium oxide.

In order to obtain a coprecipitate from the solution of the mixture of the zirconium salt and the titanium salt, alkali can be used. An alkali for use in the present invention includes an alkali metal hydroxide such as sodium hydroxide, aqueous ammonia and the like.

The pH value is adjusted to preferably 6.5 or more, more and preferably 7.0 to 9.0 in the above-mentioned process.

Then, the coprecipitate is heated to give the zirconium-titanium double oxide catalyst. The heating temperature is 100° to 500° C., and preferably 200° to 400° C. The heating time is preferably 1 to 8 hours and, more preferably 3 to 6 hours.

In thus prepared zirconium-titanium oxide catalyst, the atomic molar ratio of zirconium to titanium is equivalent to that of the zirconium salt to the titanium salt.

Hereinafter the method of preparing alcohol of the present invention will be described in detail.

In the method of preparing an alcohol of the present invention, a carboxylic acid or a carboxylic acid derivative is preferably used. The carboxylic acid or the carboxylic acid derivative is an aliphatic or an aromatic carboxylic acid or carboxylic acid derivative having 1 to 18 carbon atoms. The aliphatic carboxylic acid or carboxylic acid derivative may be saturated or unsaturated and a straight or a branched chain. The aliphatic group and the aromatic group of the aliphatic or the aromatic carboxylic acid or carboxylic acid derivative may have a substituent such as halogen. As the carboxylic acid derivatives, there are an aliphatic or an aromatic carboxylic acid ester, a nitrile, an amide, and the like.

More specifically, there are n-valeric acid, n-hexanoic acid, n-decanoic acid, n-pentadecanoic acid, isovaleric acid, isodecanoic acid, isostearic acid, pivalic acid, 5-hexenoic acid, 10-undecenoic acid, oleic acid, benzoic acid, and the like, and an ester thereof, a nitrile thereof, and an amide thereof. These compound may have a substituent such as halogen.

In the method of the present invention, an alcohol is used as a hydrogen source. The alcohol is not particularly restricted as long as it is a primary or a secondary alcohol, with a lower alcohol being preferable. From the aspects of a cost and efficiency, 2-propanol is preferable.

Hereinbelow, a gas-solid phase reaction will be described as the method of the present invention. However, it should not be construed as limiting the scope of the present invention.

First, a starting carboxylic acid or a derivative thereof is mixed with an alcohol used as a hydrogen source to prepare a mixture solution. In order to dissolve the starting material, an inert solvent such as 1,4-dioxane may be added in an appropriate amount. The mixed proportion of the carboxylic acid or the derivative thereof to the alcohol used as a hydrogen source is in the range of 1:5 to 1:500 in terms of the molar ratio.

The present invention can be carried out by a gas-solid phase reaction using an apparatus shown in the schematic view of FIG. 1. A reaction tube 1 uniformly filled with a zirconium-titanium oxide catalyst is placed in a heater 2 such as an electric furnace, and heated to 200° to 450° C., preferably 200° to 350° C. Then, the above-prepared mixture solution consisting of the starting material and the alcohol is continuously fed into the reaction tube 1 with a carrier gas via an inlet 3 attached to the reaction tube 1 through a microfeeder (not shown). As the carrier gas, an inert gas such as nitrogen, argon, and helium can be used. In the reaction tube 1, the carboxylic acid or the carboxylic acid derivative is converted into the corresponding alcohol by reduction in the presence of the zirconium-titanium oxide catalyst.

The supply rate of the mixture solution is not restricted as long as a reaction is satisfactorily proceeded, but 5 to 10 ml/hour is preferable.

The reaction product 5 coming out from the reaction tube 1, and passing through a tube 4, is led into a container 7 is cooled by an appropriate refrigerant 6 such as water and ice, and condensed in container 7. As the container 7 is connected to the tube 4 by a connecting joint 8, the container 7 can be readily disconnected from the tube 4. The carrier gas goes out from a tube 9 which is attached to the other portion of the container 7. An obtained reaction product 5 is purified by use of an appropriate means such as fractional distillation, to thereby obtain the desired alcohol.

The present invention can be carried out not only using the above-mentioned gas-solid phase reaction, but also using a heterogeneous liquid phase reaction. For example, a reaction of a mixture of a carboxylic acid or a carboxylic acid derivative and an alcohol used as a hydrogen source in the presence of the zirconium-titanium oxide catalyst is performed in a pressureapplicable container such as an autoclave, thereby obtaining the corresponding alcohol. This liquid phase reaction is suited for the reaction in which a solvent such as hydrocarbon having a higher boiling point than the reaction temperature is employed.

EXAMPLES

Hereinbelow, the present invention will be described with reference to Examples, which should not be construed as limiting the scope of the present invention.

Preparation of a catalyst

1. Preparation of catalyst A

[zirconium:titanium=1:0.5 (atomic molar ratio)]

100 g (0.310 mol) of oxyzirconium chloride (octahydrate) and 29.44 g (0.1552 mol) of titanium tetrachloride (anhydride) were dissolved in deionized water (15 l). Aqueous ammonia was gradually added thereto while stirring and adjusting the pH value to 8.6. A produced gel was collected by filtration, and then washed with deionized water. The resultant gel was spread onto a glass plate and dried at room temperature. This gel was classified, and the gel in a particle size of 24 to 60 mesh was collected and then subjected to heating in an electric furnace at 300° C. for 5 hours. A catalyst A was thus prepared.

2. Preparation of catalyst B

[zirconium:titanium=1:0.3 (atomic molar ratio)]

Catalyst B was prepared in substantially the same procedure as in the preparation of catalyst A except that 42.0 g (0.130 mol) of oxyzirconium chloride (octahydrate) and 7.46 g (0.0393 mol) of titanium tetrachloride (anhydride) were used and the pH value was adjusted to 7.1.

3. Preparation of catalyst C

[zirconium:titanium=1:0.5 (atomic molar ratio)]

Catalyst C was prepared in substantially the same procedure as in the preparation of catalyst A except that 25.01 g (0.0776 mol) of oxyzirconium chloride (octahydrate) and 7.361 g (0.0388 mol) of titanium tetrachloride (anhydride) were used and the pH value was adjusted to 7.4.

4. Preparation of catalyst D

[zirconium:titanium=1:0.7 (atomic molar ratio)]

Catalyst D was prepared in substantially the same procedure as in the preparation of catalyst A except that 32.2 g (0.100 mol) of oxyzirconium chloride (octahydrate) and 13.3 g (0.0701 mol) of titanium tetrachloride (anhydride) were used and the pH value was adjusted to 7.0.

5. Preparation of catalyst E

[zirconium:titanium=1:1 (atomic molar ratio)]

Catalyst E was prepared in substantially the same procedure as in the preparation of catalyst A except that 25.01 g (0.0776 mol) of oxyzirconium chloride (octahydrate) and 14.72 g (0.0776 mol) of titanium tetrachloride (anhydride) were used and the pH value was adjusted to 7.3.

6. Preparation of catalyst F

[zirconium:titanium=1:0.5 (atomic molar ratio)]

Catalyst F was prepared in substantially the same procedure as in the preparation of catalyst A except that sodium hydroxide was used in place of ammonia and the pH value was adjusted to 7.0.

7. Preparation of catalyst G

[zirconium:titanium=1:0.5 (atomic molar ratio)]

Catalyst G was prepared in substantially the same procedure as in the preparation of catalyst F except that 36.7 g (0.1139 mol) of oxyzirconium chloride (octahydrate) and 10.8 g (0.0569 mol) of titanium tetrachloride (anhydride) were used and the pH value was adjusted to 8.6.

EXAMPLE 1

The above prepared catalyst A (2 g) was uniformly charged in a glass tube having an inner diameter of 6.5 mm and a length of 50 cm. This tube was placed in an electric furnace and the temperature of the furnace was raised to 290° C. A nitrogen gas as a carrier gas was fed to this tube at a flow rate of 1 ml/sec. Then, a 2-propanol solution of decanoic acid (0.2 mol/l), which has been previously prepared, was supplied to a reaction tube at a flow rate of 5 ml/hour by means of a microfeeder. A reaction product coming out from the reaction tube with the carrier gas was led outside of the furnace and ice-cooled, thereby collecting the product in liquid form. Analysis of the product was performed by means of gas chromatography in comparison with a standard material. At the same time, a conversion rate of decanoic acid and a yield of decanol were measured, which were 100% and 90%, respectively.

EXAMPLES 2–4

An alcohol was produced in substantially the same procedure as in Example 1 except that use was made of catalysts shown in Table 1 and water or ice for liquefaction of the product. The results are shown in Table 1.

TABLE 1

| Example | Catalyst (atomic molar ratio; Zr:Ti) | Carboxylic acid | Conversion (%) | Product | Yield (%) |
|---|---|---|---|---|---|
| 2 | B (1:0.3) | decanoic acid | 100 | decanol | 56 |
| 3 | C (1:0.5) | decanoic acid | 100 | decanol | 81 |
| 4 | D (1:0.7) | decanoic acid | 100 | decanol | 66 |

EXAMPLE 5

Decanol was produced in substantially the same procedure as in Example 1 except that catalyst E was used and the temperature was changed to 300° C. A conversion rate of decanoic acid and a yield of decanol were measured by means of gas chromatography, which were 100% and 45%, respectively.

EXAMPLES 6 AND 7

An alcohol was produced in substantially the same procedure as in Example 1 except that use was made of catalysts shown in Table 2 and water or ice for liquefaction of the product. The results are shown in Table 2.

TABLE 2

| Example | Catalyst (atomic molar ratio; Zr:Ti) | Carboxylic acid | Conversion (%) | Product | Yield (%) |
|---|---|---|---|---|---|
| 6 | F (1:0.5) | decanoic acid | 100 | decanol | 78 |
| 7 | G (1:0.5) | decanoic acid | 100 | decanol | 90 |

EXAMPLE 8

An alcohol was produced in substantially the same procedure as in Example 1 except that catalyst A (4 g) and a solution of 10-undecenoic acid in 2-propanol (0.05 mol/l) were used, the supply rate of the mixed solution was 10 ml/hour, and the reaction temperature was changed to 250° C. A conversion rate of 10-undecenoic and a yield of 10-undecenol were measured by means of gas chromatography, which were 100% and 71%, respectively.

EXAMPLE 9

A reaction was performed in substantially the same procedure as in Example 8 except that methyl 10-undecenoate was used. A conversion rate of methyl 10-undecenoate and a yield of 10-undecenol were measured by means of gas chromatography, which were 100% and 70%, respectively.

EXAMPLE 10

A reaction was performed in substantially the same procedure as in Example 1 except that undecanenitrile was used and the reaction temperature was changed to 255° C. A conversion rate of undecanenitrile and a yield of undecanol were measured by means of gas chromatography, which were 73% and 55%, respectively.

EXAMPLE 11

A reaction was performed in substantially the same procedure as in Example 8 except that methyl tetradecanoate was used. A conversion rate of methyl tetradecanoate and a yield of tetradecanol were measured by means of gas chromatography, which were 100% and 78%, respectively.

EXAMPLE 12

A reaction was performed in substantially the same procedure as in Example 8 except that methyl hexadecanoate was used. A conversion rate of methyl hexadecanoate and a yield of hexadecanol were measured by means of gas chromatography, which were 100% and 72%, respectively.

EXAMPLE 13

A reaction was performed in substantially the same procedure as in Example 8 except that methyl octadecanoate was used. A conversion rate of octadecanoate and a yield of octadecanol were measured by means of gas chromatography, which were 100% and 49%, respectively.

EXAMPLE 14

A reaction was performed in substantially the same procedure as in Example 8 except that methyl 9-octadecanoate was used. A conversion rate of methyl 9-octadecanoate and a yield of 9-octadecen-1-ol were measured by means of gas chromatography, which were 100% and 58%, respectively.

COMPARATIVE EXAMPLES

In order to compare the method of the present invention, with the method of the prior art a hydrous zirconium oxide catalyst was used in place of the zirconium-titanium oxide catalyst used in the method of the present invention.

COMPARATIVE EXAMPLE 1

A reaction was performed in substantially the same procedure as in Example 1 except that hydrous zirconium oxide catalyst was used in place of zirconium-titanium oxide catalyst A, and that the reaction temperature was changed to 300° C. The results are shown in Table 3 below.

COMPARATIVE EXAMPLE 2

A reaction was performed in substantially the same procedure as in Example 8 except that a solution of 10-undecenoic acid in 2-propanol (0.1 mol/l) and a hydrous zirconium oxide catalyst (2 g) were used, that a supply rate was 5 ml/hour, and that the reaction temperature was changed to 300° C. The results are shown in Table 3 below.

TABLE 3

| Comparative example | Catalyst (atomic molar ratio; Zr:Ti) | Carboxylic acid | Conversion (%) | Product | Yield (%) |
| --- | --- | --- | --- | --- | --- |
| 1 | hydrous zirconium oxide (1:0) | decanoic acid | 100 | decanol | 34 |
| 2 | hydrous zirconium oxide (1:0) | 10-undecenoic acid | 95 | 10-undecenol | 10 |

What is claimed is:

1. A method of preparing an alcohol from a carboxylic acid having 1 to 18 carbon atoms or an ester, nitrile or amide derivative thereof, comprising reacting said carboxylic acid or derivative thereof and an alcohol as a hydrogen source in the presence of a zirconium-titanium double oxide catalyst having an atomic molar ratio of zirconium to titanium in the range of 1:0.3 to 1:1.0, to thereby hydrogenate said carboxylic acid or derivative thereof.

2. The method of preparing an alcohol according to claim 1, wherein said reaction is performed in a gas-solid phase reaction by feeding a mixture of said carboxylic acid or derivative thereof and said alcohol used as a hydrogen source into a reaction tube containing said catalyst uniformly.

3. The method of preparing an alcohol according to claim 1, wherein said reaction of a mixture of said carboxylic acid or derivative thereof and said alcohol used as a hydrogen source in the presence of said catalyst is performed in a gas-solid phase reaction.

4. The method of preparing an alcohol according to claim 1, wherein said carboxylic acid derivative is selected from the group consisting of a carboxylic acid ester and a nitrile.

5. The method of preparing an alcohol according to claim 1, wherein said carboxylic acid or derivative thereof is a saturated or unsaturated straight or branched aliphatic carboxylic acid having 1 to 19 carbon atoms or derivative thereof, or an aromatic carboxylic acid having 1 to 19 carbon atoms or derivative thereof, wherein said aliphatic carboxylic acid or derivative thereof and said aromatic carboxylic acid or derivative thereof may be substituted by halogen, and is selected from the group consisting of n-valeric acid, n-hexanoic acid, n-decanoic acid, n-pentadecanoic acid, isovaleric acid, isodecanoic acid, isostearic acid, pivalic acid, 5-hexenoic acid, 10-undecenoic acid, oleic acid, benzoic acid, and an ester, nitrile or amide derivative thereof, which may be substituted by halogen.

6. The method according to any one of claims 1 to 3, wherein said carboxylic acid or derivative thereof and said alcohol used as a hydrogen source are mixed in a molar ratio ranging from 1:5 to 1:500.

7. The method according to claim 1, wherein said zirconium-titanium oxide catalyst is prepared by dissolving zirconium salt and titanium salt in a solvent, adding an alkali to obtain a coprecipitate of zirconium hydroxide and titanium hydroxide, drying and heating said obtained coprecipitate at a temperature of 100° to 500° C. for 1 to 8 hours to obtain said zirconium-titanium oxide catalyst.

8. The method according to claim 7, wherein the zirconium salt is selected from the group consisting of oxyzirconium chloride, oxyzirconium acetate, zirconium chloride and zirconium nitrate.

9. The method according to claim 7, wherein the titanium salt is titanium chloride.

10. The method according to claim 7, wherein the alkali is an alkali metal hydroxide.

11. The method according to claim 10, wherein the alkali metal hydroxide is selected from the group consisting of sodium hydroxide and aqueous ammonia.

12. The method according to claim 7, wherein the coprecipitate is heated at 200° to 400° C. for 3 to 6 hours.

13. The method according to claim 1, wherein said alcohol is a secondary alcohol.

14. The method according to claim 1, wherein said alcohol is 2-propanol.

15. The method according to claim 2, wherein said reaction tube is heated to 200° to 350° C.

16. The method according to claim 2, wherein said mixture of carboxylic acid or derivative thereof and alcohol is fed into said reaction tube with an inert carrier gas consisting essentially of an inert gas selected from the group consisting of nitrogen, argon and helium.

17. A method of preparing an alcohol by converting oleic acid, or an ester, nitrile or amide derivative thereof into its corresponding alcohol, comprising reacting said oleic acid or derivative thereof and an alcohol as a hydrogen source in the presence of a zirconium-titanium double oxide catalyst having an atomic molar ratio of zirconium to titanium in the range of 1:0.3 to 1:1.0.

18. A method of preparing an alcohol from a carboxylic acid or derivative thereof selected from the group consisting of n-valeric acid, n-hexanoic acid, n-decanoic acid, n-pentadecanoic acid, isovaleric acid, isodecanoic acid, isostearic acid, pivalic acid, 5-hexenoic acid, 10-undecenoic acid, oleic acid, benzoic acid, and an ester or nitrile derivative thereof, which may be substituted by halogen, comprising reacting said carboxylic acid or derivative thereof and a primary or secondary alcohol as a hydrogen source in the presence of a zirconium-titanium double oxide catalyst having an atomic molar ratio of zirconium to titanium in the range of 1:0.3 to 1:1.0, to thereby hydrogenate said carboxylic acid or derivative thereof.

* * * * *